(12) United States Patent
Park

(10) Patent No.: US 8,888,808 B1
(45) Date of Patent: Nov. 18, 2014

(54) SLEEPING MASSAGE PAD COMPRISING A REMOVABLE SEMI-CYLINDRICAL SHAPED ACUPRESSURE SUPPORT AND AN ACUPRESSURE PAD

(71) Applicant: Byung Soo Park, Forest Hills, NY (US)

(72) Inventor: Byung Soo Park, Forest Hills, NY (US)

( * ) Notice: Subject to any disclaimer, the term of this patent is extended or adjusted under 35 U.S.C. 154(b) by 0 days.

(21) Appl. No.: 14/170,092

(22) Filed: Jan. 31, 2014

(51) Int. Cl.
*A61B 17/00* (2006.01)
*A61H 39/04* (2006.01)

(52) U.S. Cl.
CPC ...................................... *A61H 39/04* (2013.01)
USPC .......................................... 606/204; 601/134

(58) Field of Classification Search
CPC ....... A61B 17/1325; A61F 5/30; A61M 39/00
USPC .................. 606/189, 201, 204; 601/134, 135
See application file for complete search history.

(56) References Cited

U.S. PATENT DOCUMENTS

| 2,917,043 | A | * | 12/1959 | Murphy .......................... 601/58 |
| 5,158,073 | A | * | 10/1992 | Bukowski ....................... 601/28 |
| 5,250,067 | A |   | 10/1993 | Gelfer et al. |
| 7,013,588 | B2 |  | 3/2006  | Chang |

* cited by examiner

*Primary Examiner* — Victor Nguyen
(74) *Attorney, Agent, or Firm* — Im IP Law PLLC; C. Andrew Im

(57) ABSTRACT

A sleeping massage pad having a removable semi-cylindrical shaped acupressure support, an acupressure pad and a pair of mated connectors. The acupressure pad includes a neck section, a shoulder section and a back section. Each section of the acupressure pad having a plurality of different sized protrusions configured to apply acupressure with the protrusions being generally same sized within the same section. The pair of mated connectors removable connect the acupressure pad and the removable semi-cylindrical shaped acupressure support to each other.

20 Claims, 8 Drawing Sheets

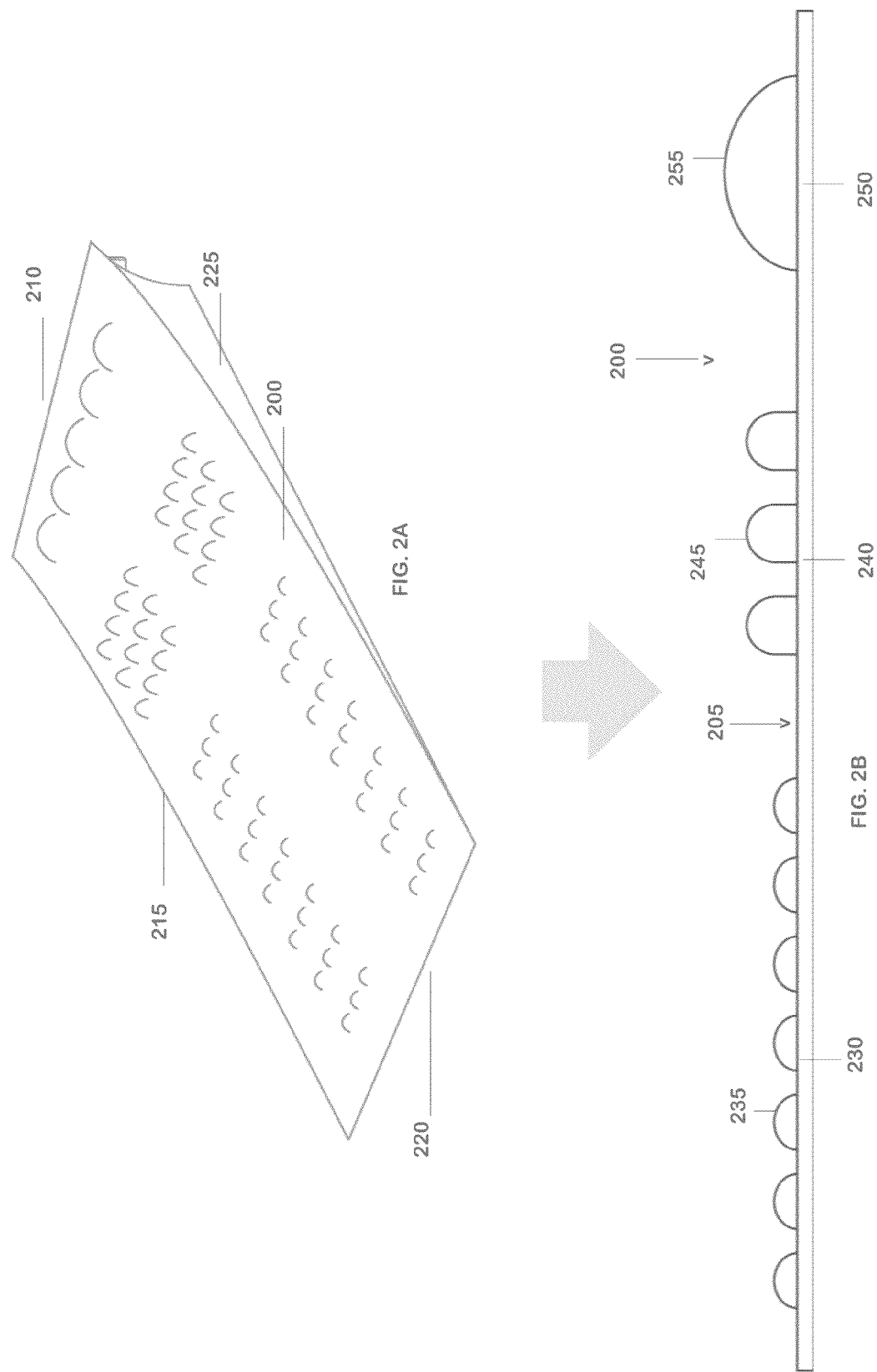

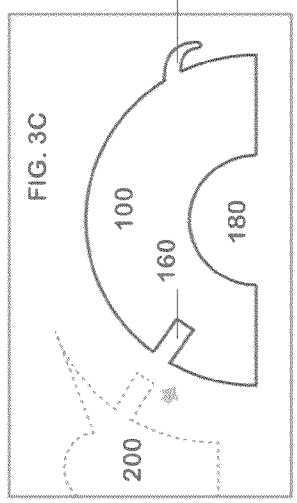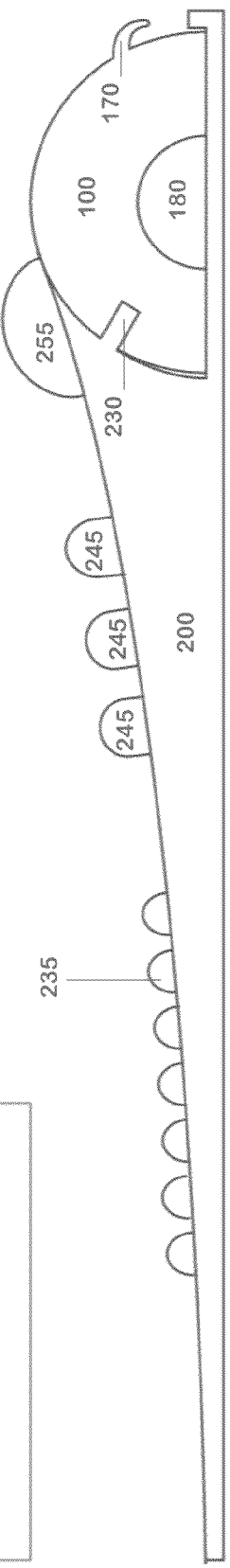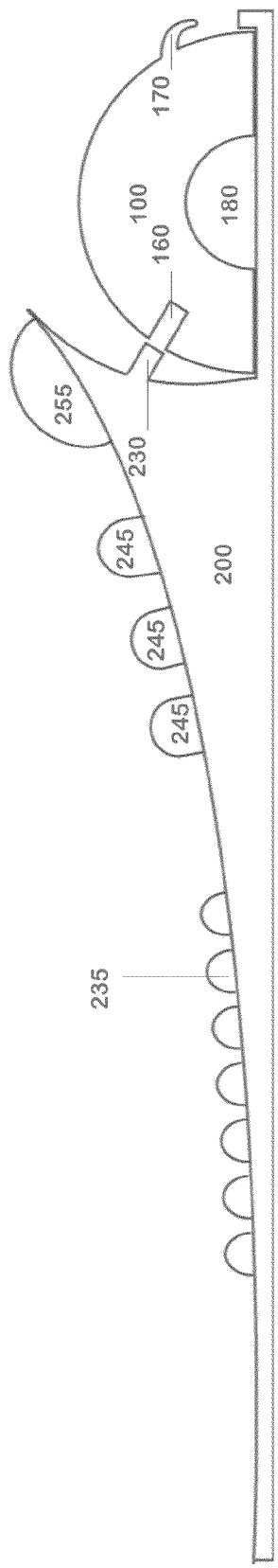

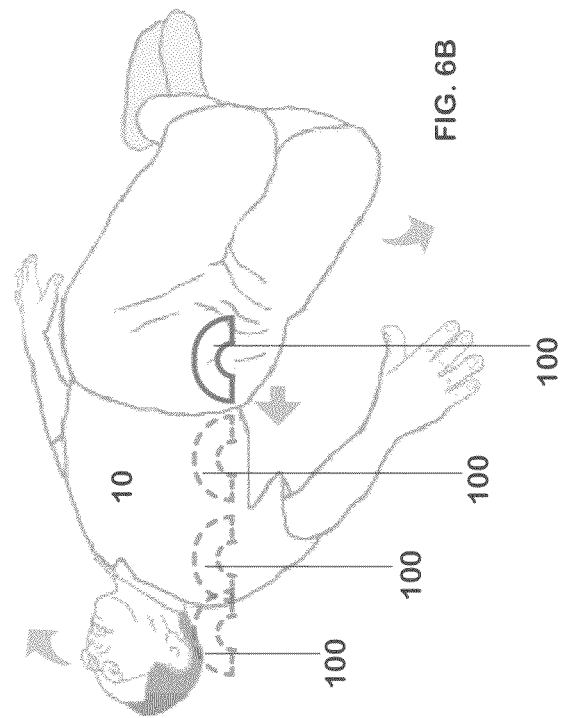
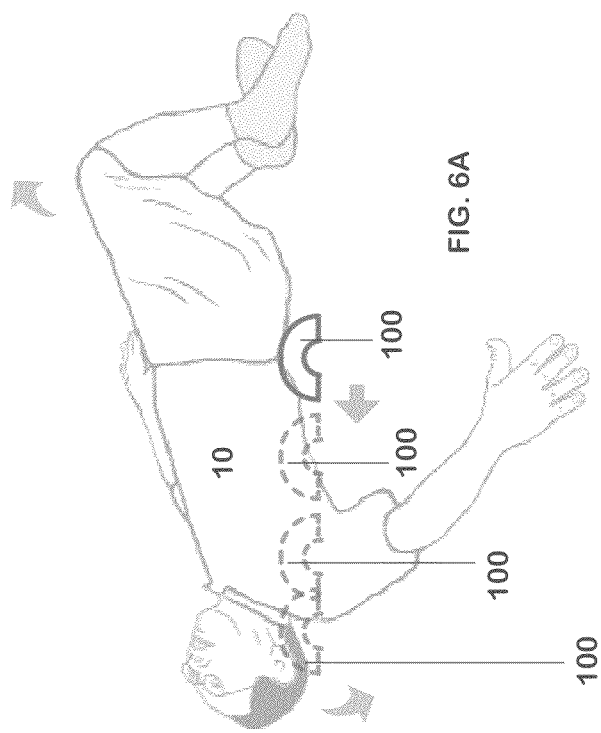

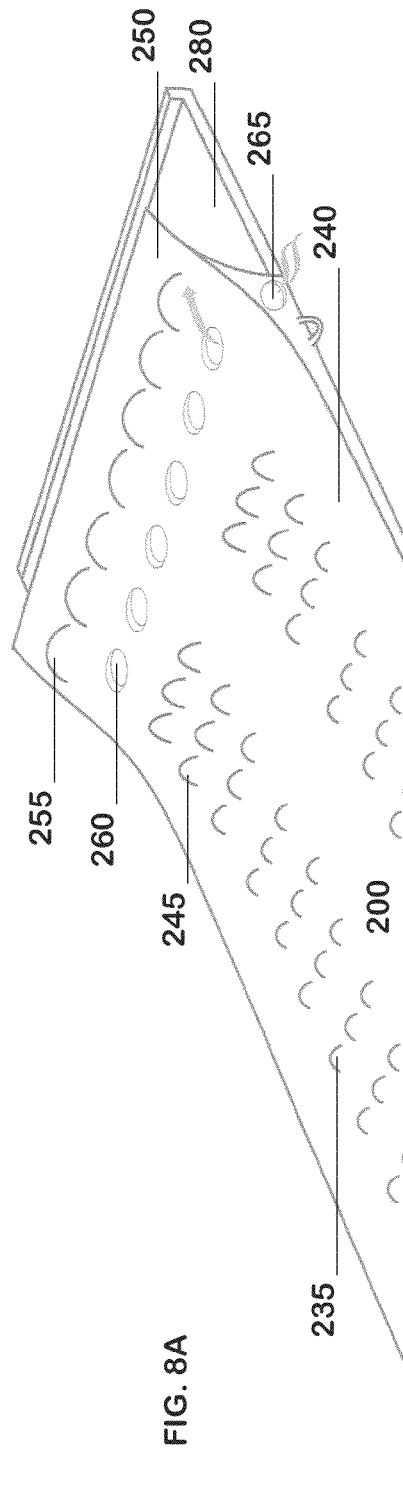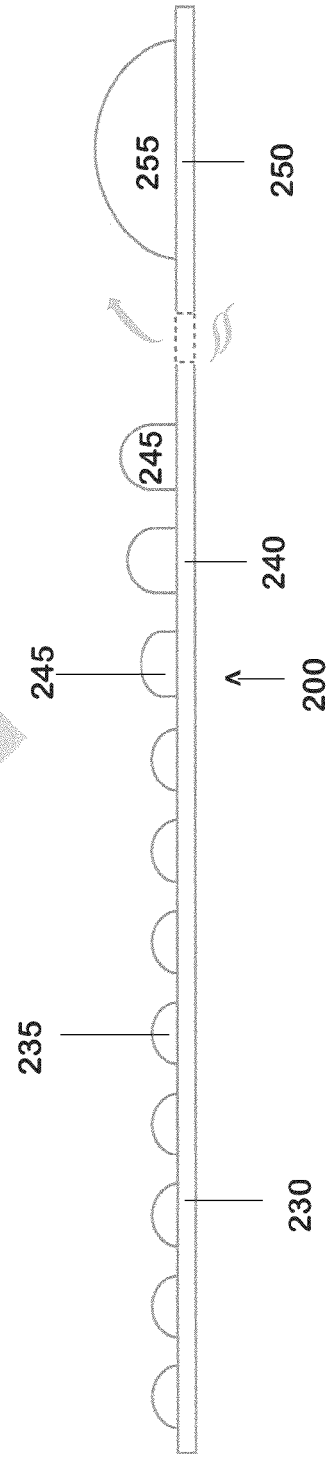
FIG. 8A
FIG. 8B

SLEEPING MASSAGE PAD COMPRISING A REMOVABLE SEMI-CYLINDRICAL SHAPED ACUPRESSURE SUPPORT AND AN ACUPRESSURE PAD

TECHNICAL FIELD

The claimed invention relates to a sleeping massage pad, and more particularly, to a sleeping massage pad that simulates the benefits of acupuncture without the association of acupuncture needles.

BACKGROUND OF THE INVENTION

Acupuncture is a collection of procedures involving penetration of the skin with needles to stimulate certain points on the body. it is believed that stimulating specific acupuncture points corrects imbalances in the flow of "qi" through channels known as meridians. Although acupuncture is relatively safe when administered by qualified practitioners using sterile needles and carries a very low risk of serious adverse effects, many people shun away from acupuncture procedures because of their fear of the acupuncture needles which penetrates their skin.

U.S. Pat. No. 5,250,067 describes an acupuncture treatment pad with multiple rigid needle-like or sharpened knife-like protuberances which penetrates a person's skin and used for short time, on the order of one to three minutes. The rigid needle-like or sharpened protuberances penetrates the user's skin and does not alleviate people fear of acupuncture procedures.

Accordingly, the claimed invention proceeds on the desirability of providing a sleeping massage pad which simulates the benefits of acupuncture without the association of needles or an object penetrating one's skin.

OBJECT AND SUMMARY OF THE INVENTION

Therefore, it is an object of the claimed invention to solve the aforementioned problems with the currently available acupuncture procedures.

Another object of the claimed invention is to provide a sleeping massage pad which provides the benefits of acupuncture without the association of needles.

A further object of the claimed invention is to provide aforesaid sleeping massage pad with a removable semi-cylindrical shaped acupressure support and an acupressure pad.

In accordance with an exemplary embodiment of the claimed invention, the sleeping massage pad comprises In accordance with an exemplary embodiment of the claimed invention, the aforesaid sleeping massage pad further comprises.

In accordance with an exemplary embodiment of the claimed invention, the aforesaid sleeping massage pad further comprises Various other objects, advantages and features of the claimed invention will become readily apparent from the ensuing detailed description. Novel features will be emphatically pointed out in the appended claims.

BRIEF DESCRIPTION OF THE DRAWINGS

The claimed invention is further explained in the description which follows with reference to the drawings, illustrations illustrating, by way of non-limiting examples, various embodiments of the invention, with like reference numerals representing similar parts throughout the several views, and wherein:

FIGS. 2A-B show perspective view and side view of the acupressure pad of FIG. 1 in accordance with an exemplary embodiment of the claimed invention;

FIGS. 3A-C show perspective views of the removable semi-cylindrical shaped acupressure support in various engagement state with the acupressure pad to form the sleeping massage pad in accordance with an exemplary embodiment of the claimed invention

FIG. 6A-B show perspective views of the removable semi-cylindrical shaped acupressure support being utilized by a user in accordance with an exemplary embodiment of the claimed invention;

FIGS. 8A-B show perspective view and side view of the acupressure pad of FIG. 7 in accordance with an exemplary embodiment of the claimed invention.

DETAILED DESCRIPTION OF THE EMBODIMENTS

Figure 1:
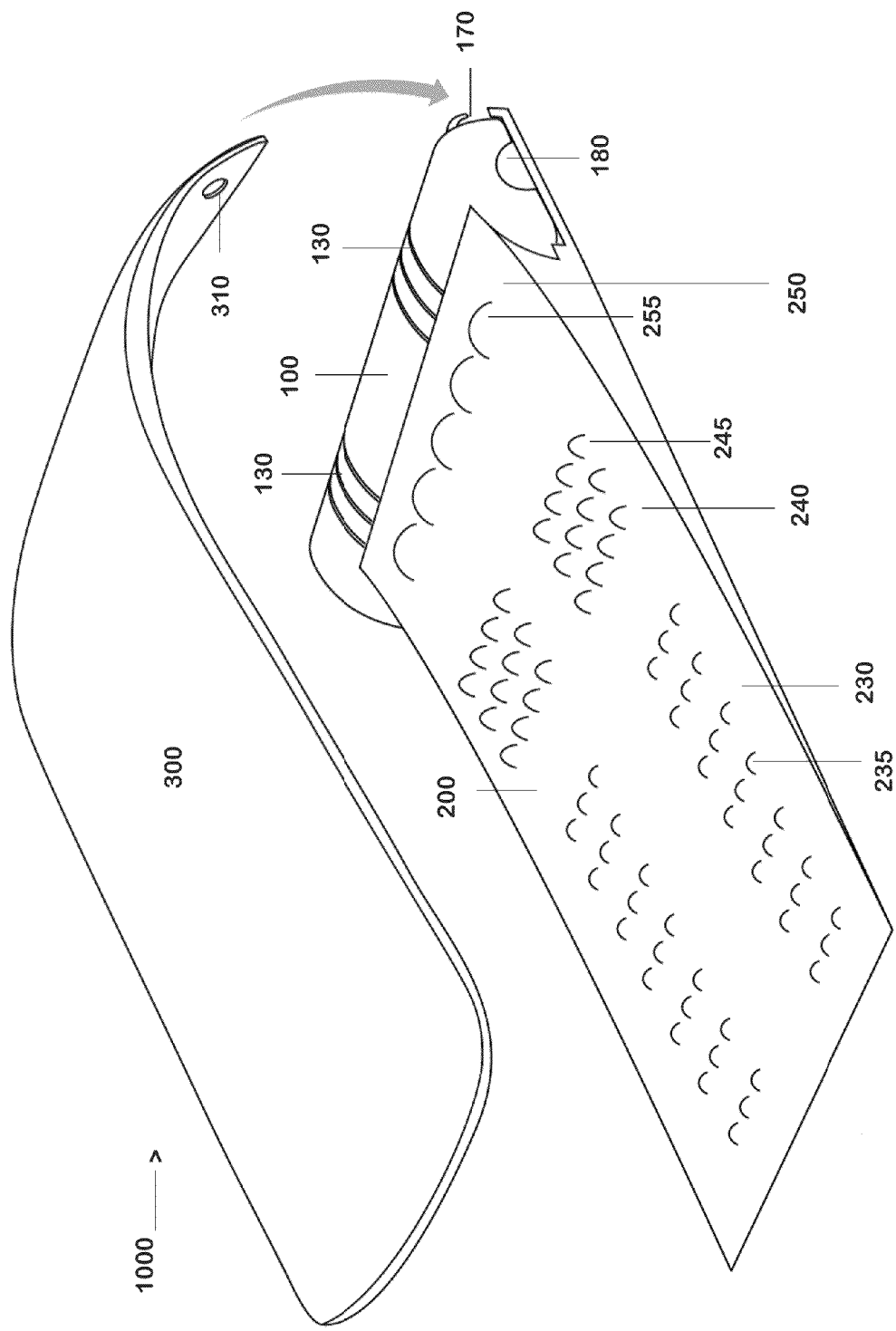
FIG. 1 shows a perspective view of the sleeping massage pad in accordance with an exemplary embodiment of the claimed invention and comprising a removable cover, a removable semi-cylindrical shaped acupressure support and an acupressure pad.

As illustrated in FIG. 1, in accordance with an exemplary embodiment of the claimed invention, the sleeping massage pad 1000 comprises a removable semi-cylindrical shaped acupressure support 100, an acupressure pad 200, and an optional removable cover 300. Preferably, as shown in FIGS. 1-4 and 7-8, the acupressure pad 200 is sloped from a thick end 210 and a thin end 220.

Figure 5:
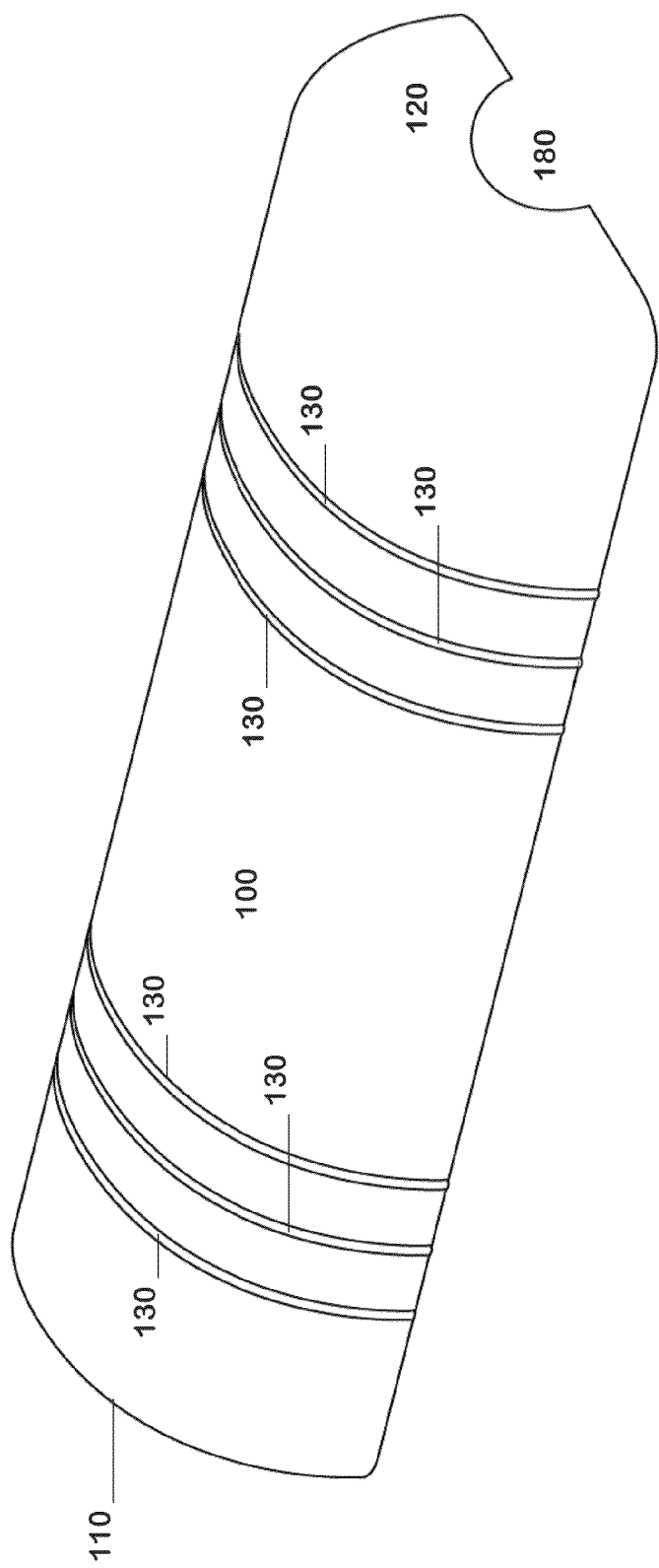
FIG. 5 shows a perspective view of the removable semi-cylindrical shaped acupressure support in accordance with an exemplary embodiment of the claimed invention.

In accordance with an exemplary embodiment of the claimed invention, the removable semi-cylindrical shaped acupressure support 100 comprises two ends 110, 120 and at least two sets of a plurality of embossed parts 130, e.g., three lines of embossed parts 130 as shown in FIG. 5. Preferably, a set of embossed parts 130 are located toward each end 110, 120 of the removable semi-cylindrical shaped acupressure support 100. It is appreciated that blood vessels are located on both sides of the human spine and as shown in FIGS. 6A-B, the embossed parts 130 apply acupressure to the spine and surrounding blood vessels when the user's body moves around the removable semi-cylindrical shaped acupressure support 100 positioned underneath the user's upper or lower back area to provide acupuncture effects. This advantageously enables the user 10 to identify and locate the pressure points on her back, thereby permitting the embossed part 130 to apply acupressure to these pressure points to strengthen and improve the functions of the user's organs, such as the heart, stomach, lung, kidney and pancreas. Similarly, when the removable semi-cylindrical shapes acupressure support 100 is positioned underneath user's shoulders and neck area and the embossed parts 130 apply acupressure to the neck and shoulder areas when the user's body moves around the removable semi-cylindrical shaped acupressure support 100.

Figure 4:
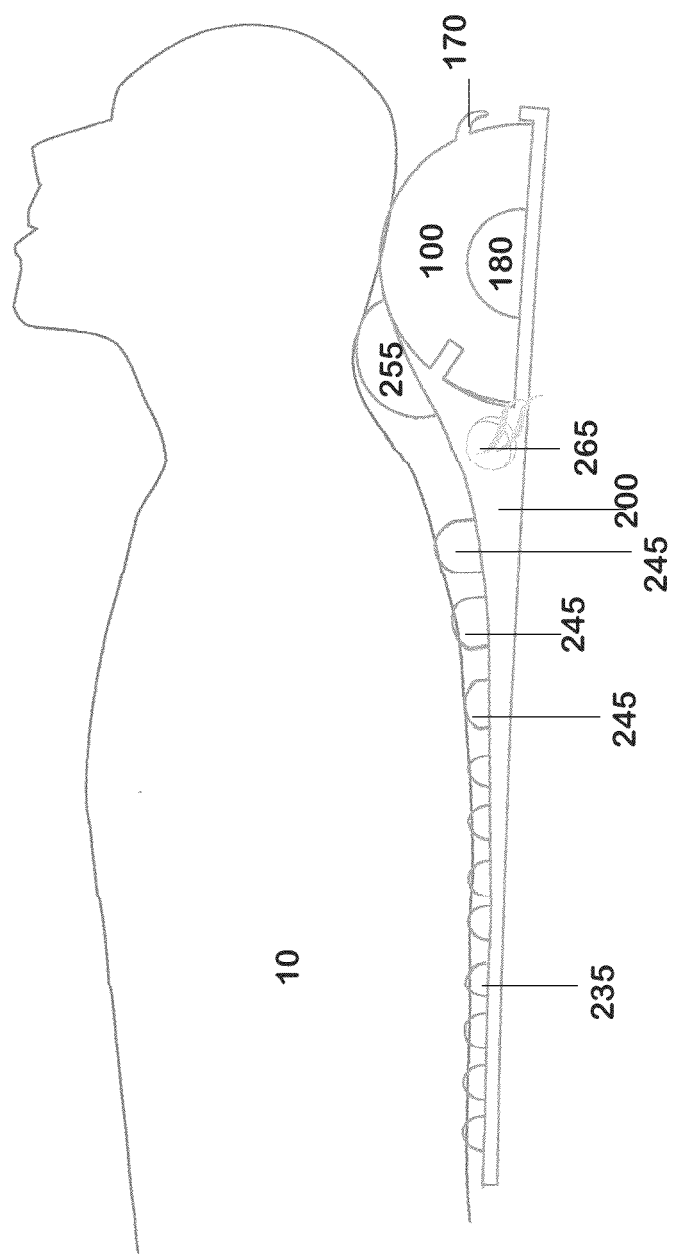
FIG. 4 shows the side view of the sleeping massage pad being utilized by a user in accordance with an exemplary embodiment of the claimed invention.
Figure 7:
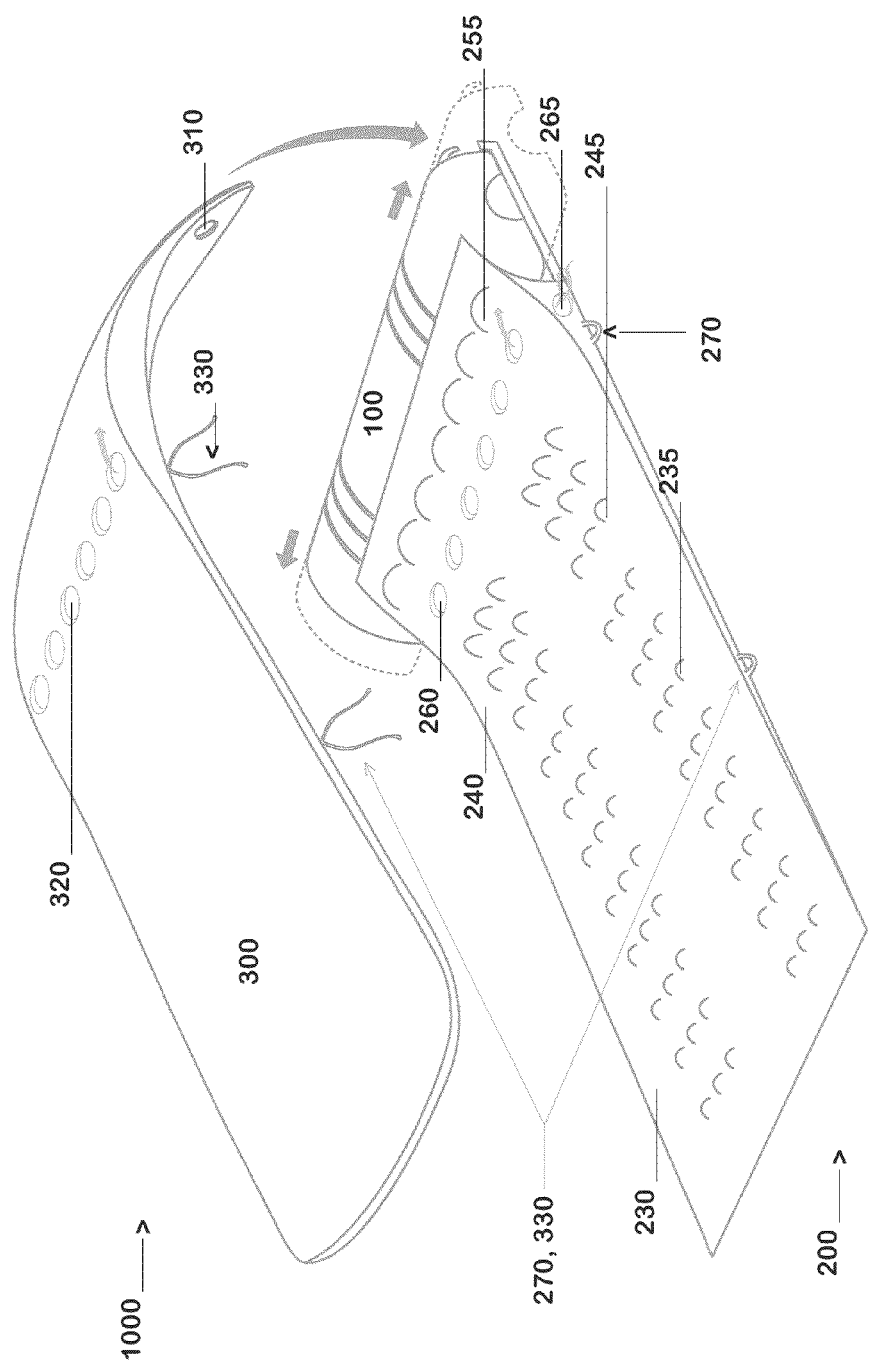
FIG. 7 shows a perspective view of the sleeping massage pad in accordance with an exemplary embodiment of the claimed invention and comprising a removable cover, a removable semi-cylindrical shaped acupressure support and an acupressure pad.

In accordance with an exemplary embodiment of the claimed invention, as shown in FIGS. 4 and 7, the removable semi-cylindrical shaped acupressure support 100 can be used to apply acupressure to the head, neck, shoulder and back areas of the user. As shown in FIGS. 6A-B, the removable semi-cylindrical shaped acupressure support 100 boosts metabolism of five major internal organs (liver, kidney, stomach, lungs and heart) when utilized by the user to apply acupressure to her neck, shoulder, upper back and lower back areas. In accordance with an exemplary embodiment of the claimed invention, the user 10 moves from side to side while moving the removable semi-cylindrical shaped acupressure support 100 from the lower back area to the neck area and vice-versa. Preferably, the removable semi-cylindrical shaped acupressure support 100 comprises an opening 180 at each 110, 120 to operate as a handle to facilitate movement of the removable semi-cylindrical shaped acupressure support 100 from one area of the body to another area of the body, as exemplary shown in FIGS. 6A-6B. That is, the removable semi-cylindrical shaped acupressure support 100 boost the metabolism of the user's internal organs by applying acupressure to the user's back spots from the user's lower back area to the upper back area when the user's body repeatedly moves from one end to the other end of the removable semi-cylindrical shaped acupressure support 100.

In accordance with an exemplary embodiment of the claimed invention, as shown in FIGS. 3A-3C, the thick end 210 of the acupressure pad 200 comprises a male connector or connector protrusion 230, preferably, an elongated cylindrical or rectangular shaped protrusion. The male connector 230 mates with a correspondingly shaped connector slot or female connector 160 on the removable semi-cylindrical shaped acupressure support 100 to provide the sleeping massage pad 1000, as exemplary shown in FIG. 4. Preferably, the male connector 230 extends along the entire width of the acupressure pad 200 at the thick end 210 and the female connector 160 extends along the entire length of the removable semi-cylindrical shaped acupressure support 100. The removable semi-cylindrical shaped acupressure support 100 can be detached from the acupressure pad 200 and used separately to apply acupressure to the head, neck, shoulder and back areas of the user, as exemplary shown in FIGS. 6A-6B.

In accordance with an exemplary embodiment of the claimed invention, the removable semi-cylindrical shaped acupressure support 100 is cushioned for comfort, such as a sponge cover (not shown). The semi-cylindrical shape of the acupressure support 100 provides acupuncture effects while the user is sleeping with the acupressure support 100 because people have tendency to move their head unconsciously during sleep and inevitably move their head across the set of embossed parts 130.

In accordance with an exemplary embodiment of the claimed invention, as shown in FIGS. 1-2B, the acupressure pad 200 comprises three sections: a neck section 250, a shoulder section 240 and a back section 230. Preferably, as shown in FIGS. 1-4 and 7-8, the acupressure pad 200 is sloped from the thick end 210 and the thin end 220. That is, the acupressure pad 200 is sloped from the neck section 250 to the back section 230 such that the neck section 250 is thicker than the back section 230 to accommodate a contour of a user's body. Each section 230, 240, 250 comprises differently sized protrusions or embossed parts 235, 245 and 255, respectively, to apply acupressure to back, shoulder and neck areas of the user 10.

In accordance with an exemplary embodiment of the claimed invention, as shown in FIGS. 1-4 and 7-8, the number and the firmness of protrusions can vary in each section of the acupressure pad 200. For example, the firmness of the neck protrusions 255 can be the hardest and the firmness of back protrusions 235 can be the softest, or vice-versa. The protrusions in each section of the acupressure pad 200 are generally similar in shape, size and firmness. Preferably, the number of back protrusions 235 in the back section 230 is greater than the number of shoulder protrusions 245 in the shoulder section 240 to cover the back area of the user 10 which is larger than the shoulder area of the user 10; and the number of shoulder protrusions 245 in the shoulder section 240 is greater than the number of neck protrusions 255 in the neck section 250 to cover the shoulder area of the user 10 which is larger than the neck area of the user 10. In accordance with an aspect of the claimed invention, as shown in FIGS. 1-4 and 7-8, the acupressure pad 200 comprises seven or eight rows back protrusions 235, three rows of shoulder protrusions 245 and one row of neck protrusions. Each row of protrusions comprises five to eight protrusions.

In accordance with an exemplary embodiment of the claimed invention, as shown in FIGS. 1-4 and 7-8, the neck protrusions 255 is wider and higher than the shoulder and back protrusions 245, 235, and the shoulder protrusions 245 are higher than the back protrusions 235. As exemplary shown in FIGS. 2*b* and 8*b*, the term higher or height refers to the distance from the surface 205 of the acupressure pad 200 to the top of the protrusions 235, 245, 255.

In accordance with an exemplary embodiment of the claimed invention, the number of the neck protrusions 255 is an odd number, preferably there are seven neck protrusions 255. The neck protrusions form a single row from one side 215 of the acupressure pad 200 to the other side 225 of the acupressure pad 200. All neck protrusions 255 are generally similar in shape, size and firmness, except for the middle neck protrusion 255 which is shorter in height than rest of the neck protrusions 255 to accommodate the user's neck.

In accordance with an exemplary embodiment of the claimed invention, as shown in FIGS. 1-4 and 7-8, the neck protrusions 255 is wider and higher than the shoulder and back protrusions 245, 235, and the shoulder protrusions 245 are higher than the back protrusions 235. As exemplary shown in FIGS. 2B and 8B, the term higher or height refers to the distance from the surface 205 of the acupressure pad 200 to the top of the protrusions 234, 245, 255.

In accordance with an exemplary embodiment of the claimed invention, as shown in FIGS. 1-4 and 7-8, the acupressure pad 200 is generally rectangular in shape and comprises the two small sides corresponding to the thick end 210 and the thin end 220, and two larger sides corresponding to sides 215, 225. In accordance with an aspect of the claimed invention, the rows of back and shoulder protrusions 235, 240 are positioned towards the sides 215, 225 of the acupressure pad 200 in the back and shoulder sections 230, 240 to form two columns. It is appreciated that blood vessels are located on both sides of the human spine and the back, and the shoulder protrusions 235, 245 apply acupressure to the spine and surrounding blood vessels when the user's body moves around the acupressure pad 200. When the user lies on the acupressure pad 200, as shown in FIG. 4, the back protrusions 235 apply acupressure to the user's upper and/or lower back areas to provide acupuncture effects. This advantageously enables the user 10 to identify and locate the pressure points on her shoulders and back, thereby permitting the shoulder and back protrusions 245, 235 to apply acupressure to these pressure points to strengthen and improve the user's organ functions, such as the heart, stomach, lung, kidney and pancreas. Similarly, the shoulder and neck protrusions 245, 255 apply acupressure to the user's shoulders and neck areas to provide acupuncture effects. Preferably, as shown in FIG. 8B, the shoulder protrusions 245 varies in height. The shoulder protrusions 245 closer to the back protrusions 235 are shorter in height than the shoulder protrusions 245 closer to the neck protrusions 255.

In accordance with an exemplary embodiment of the claimed invention, as shown in FIGS. 7-8, the acupressure pad 200 comprises a plurality of connectors 270, each connector 270 mating with a corresponding connector 330 on the cover 300. One or more hooks 170 on the removable semi-cylindrical shaped acupressure support 100 mates with corresponding holes 310 on the cover 300 to securely fastened the cover to the removable semi-cylindrical shaped acupressure 100. Preferably, there are two hooks 170 near each end of the removable semi-cylindrical shaped acupressure support. As exemplary shown in FIGS. 1 and 7, the optional cover 300 can be placed over the removable semi-cylindrical shaped acupressure support 100 and the acupressure pad to minimize or reduce the acupressure applied by the protrusions 235, 245, 255 and the embossed parts 130.

In accordance with an exemplary embodiment of the claimed invention, as shown in FIGS. 7-8, the acupressure pad 200 comprises a plurality of venting holes 260, preferably six venting holes 260, connected to an air passageway 265 that spans the entire width of the acupressure pad 200. The venting holes 260 and the air passageway 265 are preferably located in the neck section 250 of the acupressure pad 200, preferably below the neck protrusions 255. The optional cover 300 also comprises corresponding venting holes 320 such that the venting holes 320 on the optional cover line up with the venting holes 260 on the acupressure pad 200 when the optional cover 300 is placed over the acupressure pad 200.

In accordance with an exemplary embodiment of the claimed invention, as shown in FIG. 8B, the acupressure pad 200 further comprises a head section 280 near the thick end 210 of the acupressure pad 200 to removably receive the removable semi-cylindrical shaped acupressure support 100. Preferably, as shown in FIG. 7, the removable semi-cylindrical shaped acupressure support 100 can move laterally on the head section 280 along the width of the acupressure pad 100. That is, the mated connectors 160, 230, connecting the removable semi-cylindrical shaped acupressure support 100 and the acupressure pad 200, are configured to enable the removable semi-cylindrical shaped acupressure support 100 to move laterally on the head section 280 from one side 215 of the acupressure pad to the other side 225 of the acupressure without disengaging.

In accordance with an exemplary embodiment of the claimed invention, the acupressure pad 200 can be made of one type of material or multiple types of material. For example, the acupressure pad 200 can be molded from various materials to provide sturdy backing or bottom surface and a cushioned top surface where the protrusions are located.

The claimed sleeping massage pad 1000 can be utilized to alleviate pain and refresh one's body through acupressure massage provided by various protrusions 235, 245, 255 and/or the embossed parts 130. The claimed invention advantageously replicates the actions of acupuncture without associated needles penetrating one's skin and improves the overall blood circulation which enhances the health of user's organs to advance the overall health of the user.

Although the claimed invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the claimed invention described in the specification.

What is claimed is:

1. A sleeping massage pad, comprising:
a removable semi-cylindrical shaped acupressure support;
an acupressure pad comprising a neck section, a shoulder section and a back section, each section of the acupressure pad comprising a plurality of different sized protrusions configured to apply acupressure with the protrusions being same sized within the same section;
a pair of mated connectors to removable connect the acupressure pad and the removable semi-cylindrical shaped acupressure support to each other;
wherein the acupressure pad further comprises a head section proximate to the neck section of the acupressure pad to removably receive the removable semi-cylindrical shaped acupressure support; and
wherein the mated connectors are configured to enable the removable semi-cylindrical shaped acupressure support to move laterally on the head section from one side of the acupressure pad to other side of the acupressure without disengaging.

2. The sleeping massage pad of claim 1, wherein the removable semi-cylindrical shaped acupressure support further comprises at least two sets of a plurality of embossed parts for applying acupressure.

3. The sleeping massage pad of claim 2, wherein each embossed part extends from one edge to other edge of the removable semi-cylindrical shaped acupressure support.

4. The sleeping massage pad of claim 2, wherein a set of embossed parts is located toward each end of the removable semi-cylindrical shaped acupressure support to apply acupressure to a user's spine and surrounding blood vessels.

5. The sleeping massage pad of claim 1, wherein the protrusions located in the neck section of the acupressure pad are larger than the protrusions located in the shoulder section of the acupressure pad.

6. The sleeping massage pad of claim 1, wherein the protrusions located in the shoulder section of the acupressure pad are larger than the protrusions located in the back section of the acupressure pad.

7. The sleeping massage pad of claim 1, wherein a number of protrusions located in the shoulder section of the acupressure pad are greater than a number of protrusions located in the neck section of the acupressure pad.

8. The sleeping massage pad of claim 1, wherein a number of protrusions located in the back section of the acupressure pad are greater than a number of protrusions located in the shoulder section of the acupressure pad.

9. The sleeping massage pad of claim 1, wherein the protrusions located in the neck section of the acupressure pad are longer than the protrusions located in the shoulder section of the acupressure pad.

10. The sleeping massage pad of claim 1, wherein the protrusions located in the shoulder section of the acupressure pad are longer than the protrusions located in the back section of the acupressure pad.

11. The sleeping massage pad of claim 1, wherein the protrusions located in the shoulder section or shoulder protrusions varies in size such that the shoulder protrusions near the neck section are larger than the shoulder protrusions near the back section.

12. The sleeping massage pad of claim 1, wherein the protrusions located in the shoulder and back sections form two columns to apply acupressure to a user's spine and surrounding blood vessels.

13. The sleeping massage pad of claim 1, wherein the acupressure pad comprises a plurality of venting holes connected to an air passageway extending from one side of the acupressure pad to other side of the acupressure pad, the venting holes and the air passageway are located near the protrusions in the neck section.

14. The sleeping massage pad of claim 1, wherein the acupressure pad is sloped from the neck section to the back section such that the neck section is thicker than the back section to accommodate a contour of a user's body.

15. The sleeping massage pad of claim 1, further comprising a cover removably attachable to the removable semi-cylindrical shaped acupressure support, the cover is configured to reduce the acupressure applied by the protrusions.

16. The sleeping massage pad of claim 15, wherein the cover and the acupressure pad comprises a plurality of mated connectors to removable connect the cover to the acupressure pad.

17. The sleeping massage pad of claim 1, wherein a number of protrusions in the neck section or neck protrusions is an odd number and the neck protrusions form a single row from one side of the acupressure pad to other side of the acupressure pad; and wherein a neck protrusion in the middle of the row is shorter than rest of the neck protrusions to accommodate a user's neck.

18. A sleeping massage pad, comprising:
   a removable semi-cylindrical shaped acupressure support;
   an acupressure pad comprising a neck section, a shoulder section and a back section, each section of the acupressure pad comprising a plurality of different sized protrusions configured to apply acupressure with the protrusions being same sized within the same section;
   a pair of mated connectors to removable connect the acupressure pad and the removable semi-cylindrical shaped acupressure support to each other;
   a cover removably attachable to the removable semi-cylindrical shaped acupressure support, the cover is configured to reduce the acupressure applied by the protrusions;
   wherein the cover and the acupressure pad comprises a plurality of mated connectors to removable connect the cover to the acupressure pad;
   wherein the acupressure pad further comprises a plurality of venting holes connected to an air passageway extending from one side of the acupressure pad to other side of the acupressure pad, the venting holes and the air passageway are located near the protrusions in the neck section; and
   wherein the cover comprises a plurality of venting holes to correspond substantially to the venting holes of the acupressure pad such that the venting holes of the cover line up with the venting holes of the acupressure pad when the cover is utilized with the acupressure pad.

19. The sleeping massage pad of claim 18, wherein the removable semi-cylindrical shaped acupressure support further comprises at least two sets of a plurality of embossed parts for applying acupressure, each embossed part extends from one edge to other edge of the removable semi-cylindrical shaped acupressure support.

20. The sleeping massage pad of claim 18, wherein the acupressure pad comprises a head section proximate to the neck section of the acupressure pad to removably receive the removable semi-cylindrical shaped acupressure support; and wherein the mated connectors are configured to enable the removable semi-cylindrical shaped acupressure support to move laterally on the head section from one side of the acupressure pad to other side of the acupressure without disengaging.

* * * * *